United States Patent [19]
Bienzle

[11] Patent Number: 5,270,037
[45] Date of Patent: Dec. 14, 1993

[54] USE OF INTERFERON AND A SUBSTANCE WITH AN ANTIMALARIAL ACTIVITY FOR THE TREATMENT OF MALARIA INFECTIONS

[75] Inventor: Ulrich Bienzle, Berlin, Fed. Rep. of Germany

[73] Assignee: Boehringer Ingelheim GmbH, Fed. Rep. of Germany

[21] Appl. No.: 974,366

[22] Filed: Nov. 9, 1992

Related U.S. Application Data

[63] Continuation of Ser. No. 800,523, Dec. 4, 1991.

[30] Foreign Application Priority Data

Jul. 12, 1990 [DE] Fed. Rep. of Germany ....... 4039114

[51] Int. Cl.$^5$ ............................................. A61K 45/02
[52] U.S. Cl. ................................. 424/85.5; 424/85.4; 424/85.6; 424/85.7
[58] Field of Search ................... 424/85.5, 85.4, 85.6, 424/85.7

[56] References Cited

U.S. PATENT DOCUMENTS 4,915,941 4/1990 Vigouroux et al. ................ 424/85.4

OTHER PUBLICATIONS

Bienzle et al., "Inhibition of *Plasmodium vinckei*-malaria in mice by recombinant murine interferon-γ", Acta Tropica 45:289–290 (1988).

Clark et al., "Inhibition of Murine Malaria (*Plasmodium chabaudi*) in Vivo by Recombinant Interferon-γ or Tumor Necrosis Factor, and its Enhancement by Butylated Hydroxyanisole", *J. Immunol.* 139(10):3493–3496 (Nov. 15, 1987).

Doberstyn et al., "Single-Dose Therapy of Falciparum Malaria Using Pyrimethamine in Combination with Diformyldapsone or Sulfadoxine", *Am. J. Trop. Med. Hyg.* 25(1):14–19 (1976).

Ferreira et al., "Inhibition of Development of Exoerythrocytic Forms of Malaria Parasites by γ–Interferon", *Science* 232:881–884 (May 16, 1986).

Hall et al., "Falciparum Malaria Cured by Quinine Followed by Sulfadoxine-Pyrimethamine", *Br. Med. J.* 2:15–17 (Apr. 5, 1975).

Heath et al., "Interferon-γ as an Adjuvant in Immunocompromised Mice", *Immunol.* 67:520–524 (1989).

Hurwitz et al., "Resistance of Plasmodium Falciparum Malaria to Sulfadoxine-Pyrimethamine ('Fansidar') in a Refugee Camp in Thailand", *Lancet* 1:1068–1070 (May 16, 1981).

Jiang et al., "Antimalarial Activity of Mefloquine and Quighaosu", *Lancet* 2:285–288 (Aug. 7, 1982).

Masheshwari et al., "Recombinant Human Gamma Interferon Inhibits Simian Malaria", *Infect. Immun.* 53(3):628–630 (Sep. 1986).

Merkli et al., "The Inhibiting Effect of a Drug Combination on the Development of Mefloquine Resistance in *Plasmodium berghei*", *Ann. Trop. Med. Parasit.* 74(1):1–9 (1980).

Playfair and Souza, "Recombinant Gamma Interferon is a Potent Adjuvant for a Malaria Vaccine in Mice", *Clin. exp. Immunol.* 67:5–10 (1987).

Shear et al., "Role of IFN-γ in Lethal and Nonlethal Malaria in Susceptible and Resistant Murine Hosts", *J. Immunol.* 143(6):2038–2044 (Sep. 15, 1989).

Stürchler, D., "Malaria prophylaxis in travellers: the current position", *Experientia* 40:1357–1362 (1984).

"Malaria prophylaxis for long term visitors", *British Medical Journal* 287:1454–1455 (Nov. 12, 1983).

Colbourne, M. J., "Malaria prophylaxis with chloroquine", *The Lancet* 2:1346 (Dec. 12, 1981).

Colbourne, M. J. and Draper, C. C., "Proguanil for malaria prophylaxis", *The Lancet* 1:1228 (May 28, 1983).

European Search Report for EP91120822 for the corresponding European application.

Bliznakov, E. G., "Potentiation of the efficacy of chloroquine in *Plasmodium berghei* infection in mice by interferon inducers", *Abstracts of the Annual Meeting of the Amer. Soc. for Microbiol.*, p. 262 (1981).

Mendis, K. N., et al., "Anti-parasite effects of cytokines in malaria", *Immunology Letters* 25:217–220 (1990).

Stevenson, M. M., et al., "Review: cytokines and malaria", *Clinical and Investigative Medicine* 13(6):353–359 (1990).

*Primary Examiner*—Schain Howard E.
*Assistant Examiner*—P. Lynn Touzeau
*Attorney, Agent, or Firm*—Sterne, Kessler, Goldstein & Fox

[57] ABSTRACT

The use of pharmaceutical compositions comprising at least one antimalarial active substance and an interferon, preferably interferon-gamma (IFN-γ), is disclosed. The pharmaceutical composition according to the invention are used in the treatment of clinical malaria.

6 Claims, 1 Drawing Sheet

USE OF INTERFERON AND A SUBSTANCE WITH AN ANTIMALARIAL ACTIVITY FOR THE TREATMENT OF MALARIA INFECTIONS

This application is a continuation of application Ser. No. 07/800,523, filed Dec. 4, 1991.

FIELD OF THE INVENTION

The present invention is in the field of medicinal chemistry. In particular, the present invention relates to the use of interferon and an active substance with an antimalarial activity for the preparation of a pharmaceutical composition for treating malaria infections in the erythrocytic (clinical) phase. The invention is characterized by the use of a pharmaceutical composition based on at least one antimalarially active substance which additionally contains an interferon, preferably interferongamma (IFN-$\gamma$). The malaria infections to be treated with the drug combination according to the invention comprise those caused by protozoa of the genus Plasmodium, e.g. those of the species *Plasmodium falciparum, Plasmodium vivax, Plasmodium malariae, Plasmodium ovale*, which are known to infect human beings preferentially, as well as *Plasmodium berghei, Plasmodium knowlesi, Plasmodium vinckei, Plasmodium cynomologi, Plasmodium chabaudi, Plasmodium yoellii*, which attack chiefly animal hosts, e.g. rodents and monkeys.

BACKGROUND OF THE INVENTION

Although malaria has been treated for decades partly by eliminating any intermediate host with insecticides and partly by therapeutic measures, this infective illness caused by various types of Plasmodium even now constitutes one of the major health problems worldwide. It is estimated that, every year, up to 200 million people living in tropical countries are infected with malaria pathogens, with lethal consequences for 1 to 2 million of those affected (Sturchler, D., *Experientia* 40:1357–1362, (1984)).

The problem of fighting malaria is chiefly that, when insecticides are used, insecticide-resistant intermediate hosts or vectors (Anopheles) occur again and again and the drug treatment, which is basically only a prophylactic, constantly allows drug-resistant protozoa (Plasmodium) to develop (Doberstyn, E. B., *Experientia* 40:1311–1317, (1984); Bruce-Chwatt, L. J., *Annu. Rev. Public Health* 8:75–110, (1987)).

Ever since the start of modern malaria research, initiated over 100 years ago with the discovery of the original pathogen causing malaria (Laveran, A., *Bull. Acad. Med. Paris* 9:1235–1236, (1980)), it has not been possible to provide an active ingredient which provides an adequate and lasting therapy for malaria infection.

The bite of the infected mosquito causes malaria parasites (sporozoites) to be transferred to humans. These sporozoites colonize the liver where they multiply. At the end of this development phase, parasites (merozoites) enter the bloodstream and attack erythrocytes. With the infection of the erythrocytes, the actual clinical phase of the illness begins with the known symptoms and complications.

For the treatment of malaria in humans and animals, which has hitherto been of a purely prophylactic nature, a number of measures have been proposed which comprise the use of antimalarial substances, immunization or vaccination and the use of cytokines.

The known antimalarial substances can be divided into the following 6 main groups on the basis of their chemical compositions:
1. the 9-aminoacridines (e.g. mepacrine),
2. the 4-aminoquinolines (e.g. amodiaquine, chloroquine, hydroxchloroquine).
3. the 8-aminoquinolines (e.g. primaquine, quinocide),
4. the biguanides with an inhibiting effect on dihydrofolic acid reductase (e.g. chloroproguanil, cycloguanil, proguanil),
5. the diaminopyrimidines (e.g. pyrimethamine),
6. the quinine salts.

In addition to these groups, sulphones such as dapsone, sulphonamides, sulphanilamides and antibiotics such as tetracycline are also used as antimalarial agents.

Depending on their mode of activity the known antimalarial agents can be divided into the following categories:
1. causal prophylactic substances effective against primary tissue stages,
2. active substances directed against relapses or recurrences and effective against latent tissue stages,
3. blood schizonticides,
4. gametocytocides and
5. sporonticides.

The first group includes, for example, proguanil, pyrimethamine and primaquine and the derivatives thereof and possibly also sulphanilamides, sulphonamides and tetracyclines. For the second group, 8-aminoquinolines such as primaquine and its analogues and derivatives are available, for example, as well as floxacrine, cycloguanil, dapsone and quinazolines. Substances active against the blood schizonts, the third category, include in particular 4-aminoacridines such as mepacrine and the 4-aminoquinolines such as chloroquine or chloroquinesulphate, quinine, amodiaquine and mepacrine, mefluquine and related compounds such as halofantrene, as well as pyrimethamine, proguanil, primaquine and the sulphanilamides and sulphonamides, particularly in conjunction with pyrimethamine.

Other substances which may be considered are the sesquiterpene lactones based on the compound artemisinine and the semisynthetic derivatives thereof such as artesunate and artemether as well as piperaquine, hydroxypiperaquine, pyronaridine, halofantrene and, generally, the biguanides and quinine salts.

The schizonticides mentioned above are effective against the gametocytes of, for example, *P. vivax, P. malariae* or *P. ovale*, but not against the mature gametocytes. The 8-aminoquinolines such as primaquine and quinocide are also effective against the gametocytes. Proguanil, primaquine and pyrimethamine may be mentioned as sporonticidal agents. Other known antimalarial agents are: chloroproguanil, cycloguanil (e.g. as a salt of embonic acid), pamaquine, plasmocide, totaquine, spirogermanium, febrifugine, brusatol, bruceine-A, bruceine-B, bruceine-C, yadanziolide-A, tebuquine, enpirolin, eurycomanone, 3-(4-imidazolyl)-2-(pivaloylamido)propionylhydrazide, cinchonidine; cucurbitacine, tripynadine, 5-ethylthioribose, arteether (ethylether analogues of artemether), artenilic acid, pyrexol, atalaphillinine, diformyldapsone, bruceantine, nitroquine, octanoylprimaquine, pyrimethamine plus sulfadoxine, hivernine, dabequine, artelinic acid, mefloquinquinate, halfantrin-beta-glycerophosphate, nimbolide, sergeolide (quassinoid of *Picrolemma pseudocoeffea*), simalikalactone-D, fluoroquine, fluorenmethanol, isouramil, cycloleucine, acedapsone (diacetyldapsone), gentiopicrine, amquinate (amquinolate), endochine, pentaquine, isopentaquine, methylchloroquine, amopyroquine, quinine, hydroquinine (dihydroquinine), dimeplasmine, azacrine, diapromine, menoctone, cycloquine (haloquine), lapinone, aristoquine, cloguanamil, clociguanil, brindoxime, cinchonine, tripiperaquine, 3-hydroxy-2-(4-(4-phenyl)-cyclohexyl)-1,4-anthraquinone, aminodiaquine, 4-methyl-5-n-pentoxyprimaquine, 4-methyl-5-n-hexoxyprimaquine, 2-(4-(4-chlorophenyl)-cyclohexyl)-3-hydroxy-1,4-naphthalenedione, gossypol derivatives, halofantrine (1,3-dichloro-a-(2-(dibutylamino)ethyl)-6-(trifluoromethyl)-9-phentantrene-methanol), cinchona alkaloids (e.g. in the combination quinine, quinidine, cinchonine), N,N'-bis(3-((phenylmethyl)amino)propyl)-1,8-octanediamine, N,N-bis(3-((phenylmethyl)amino)-propyl)-1,7-diaminoheptane, selenium-analogues of 2-acetyl and 2-propionyl-pyridinethiosemicarbazones, tebuquine, 2,6-bis(1-piperidinylmethyl)-4-((7-(trifluoromethyl)-4-quinolinyl)amino)-phenol, primary phosphoric acid esters of 4'-chloro-5-(1,1-dimethylethyl)-3-(((1,1-dimethylethyl)amino)methyl)-(1,1'-biphenyl-2-ol, N4-(2,6-dimethoxy-4-methyl-5-(3-trifluoromethyl)-phenoxy-8-quinolinyl)-1,4-pentanediamine, N,N-diethyl-N'-(6-methoxy-4-methyl-8-quinolinyl)-1,6-hexanediamine, 5-(N-aryl-tropan-3-yl)-and 5-(piperidin-4-yl)-2,4-diamino-pyrimidine, 4'-amino-4-n-propylamino-2-methyl-diphenylsulphone, 5-ethylthioribose, riboflavin-analogues,1-(3-(2,4-dichlorophenoxy)-1,6-dihydro-6,6-dimethyl-1,3,5-triazine-2,4-diamine as the monohydrobromide, 1,6-dihydro-6,6-dimethyl-1-(3-(2,4,5-trichlorophenoxy)-propoxy)-1,3,5-triazine-2,4-diamine as the monohydrochloride, trans-2-(4-(1,1-dimethylethyl)-cyclohexyl)-3-hydroxy-1,4-naphthalenedione, enpiroline, mirincamycin, tripynadine, 3-(4-imidazolyl)-2-(pivaloylamido)propionylhydrazide, 2-acetylpyridine-thiosemicarbazones and the pyrrolidine derivatives thereof.

However, the use of these substances on their own or in conjunction with one another has the disadvantage that they achieve only a preventive or only temporary effect and the pathogens in question develop resistance more or less quickly; furthermore, many of these compounds have a toxic effect or are effective only in toxic concentrations (Peters, W, Br. Med. Bull. 38:187–192, (1982); Young et al., Am. J. Trop. Med. Hyg. 10:317–320 (1961); Bygbjerg, et al., Lancet 1:21–26 (1983); Schmidt, L. H., Antimicrob. Agents Chemother 16:475–485 (1979); Bruce-Chwatt, L. J. Essential malariology, W. Heinemann Medical Books Ltd., London, (1980)).

Many of these compounds have undesirable side effects or can be administered only to certain groups of people; furthermore, the very short plasma half-life of some of these substances prevents reasonable prophylactic use (Bruce-Chwatt et al., "Chemotherapy of Malaria" (2nd ed.) WHO, Geneva (1981); Colbourne, M. J., Comm. Dis. Rep. 35:3–4 (1983); Jiang et al., Lancet 2:285–288 (1982)).

In view of the increasing resistance to the compounds mentioned above, various combinations of these substances have been used, e.g. pyrimethamine with sulphadoxine (Doberstyn et al., Am. J. Trop. Med. Hyg. 25:14–19 (1976); Hall et al., Br. Med. J. 2:15–17 (1975); Merkli et al., Ann. Trop. Med. Parasit. 74:1–9 (1980)).

However, such combinations have not solved the problem of drug resistance and in addition complications have arisen caused by side effects (Hurwitz et al., Lancet 1:1068–70 (1981); Phillips et al., Lancet 1:300–302 (1984); Björkman et al. Trans. R. Soc. Trop. Med. Hyg. 84:177–180 (1990)).

In addition to the use of antimalarial substances of this kind it has been proposed to treat malaria infection prophylactically by immunization or vaccination.

However, the use of various preparations from the different plasmodial stages (sporozoites, merozoites, schizonts, gametes) has produced unsatisfactory results, particularly as the result of undesirable autoimmune reactions and non-specific immune responses (Trager et al., Parasite Immun. 5:255 (1983); Wernsdorfer, W. H., Bull, WHO 59:335 (1981)). Hitherto, an ideal vaccine has not become available (Young, et al. TIBTECH 6:63–68 (1988)).

In addition to the above-mentioned processes, the use of interferon, e.g. interferon-gamma (IFN-$\gamma$), has been proposed both for vaccination (Playfair et al., Clin. Exp. Immunol. 67:5–10 (1987); Heath, et al., Immunol. 67:520–524 (1989)), and also for therapeutic treatment (Bienzle et al., Acta Tropica 45:289–290 (1988); Masheshwari et al., Infect. Immun. 53:628–633 (1986); Ferreira et al., Science 232:881–883 (1986); Clark et al., J. Immunol 139:3493–3496 (1987); Shear et al., J. Immunol. 143:2038–2044 (1989)).

In the former case, IFN-$\gamma$ acted as an adjuvant in conjunction with a suitable antigen; in the second case, although the development of the disease was slowed down in prophylactic use, therapeutic application, i.e. post infectionem, was less effective and was unable to inhibit the multiplication of parasites sufficiently. The combined prophylactic and therapeutic application of IFN-$\gamma$ had only a cumulative effect. There was no successful treatment in the sense of curative effect in any of the cases since all the animals (mice) died from the malaria infection when treated by any of the three methods, irrespective of how long the treatment lasted and with what dosages the animals were treated (Bienzle et al. (1988), loc. cit.).

In U.S. Pat. No. 4,915,941 it is proposed to use IFN-$\gamma$ in conjunction with an antimalarially active substance for preventing malaria infection, in which the administration of this combination does not extend beyond the prepatent phase (liver phase). During this phase it is not possible to diagnose the malaria.

SUMMARY OF THE INVENTION

Surprisingly, it has now been found that a combination consisting of interferon, particularly IFN-$\gamma$, plus at least one antimalarially effective agent is suitable for treating malaria in the erythrocytic, i.e. clinical, phase, which manages to destroy the parasites in the red blood cells (erythrocytes).

Thus, the invention is directed to a method for treating erythrocytic clinical malaria, comprising administering to an animal in need of such treatment an amount effective of an interferon and at least one additional substance having antimalarial activity.

DESCRIPTION OF THE PREFERRED EMBODIMENTS

Figure 1:
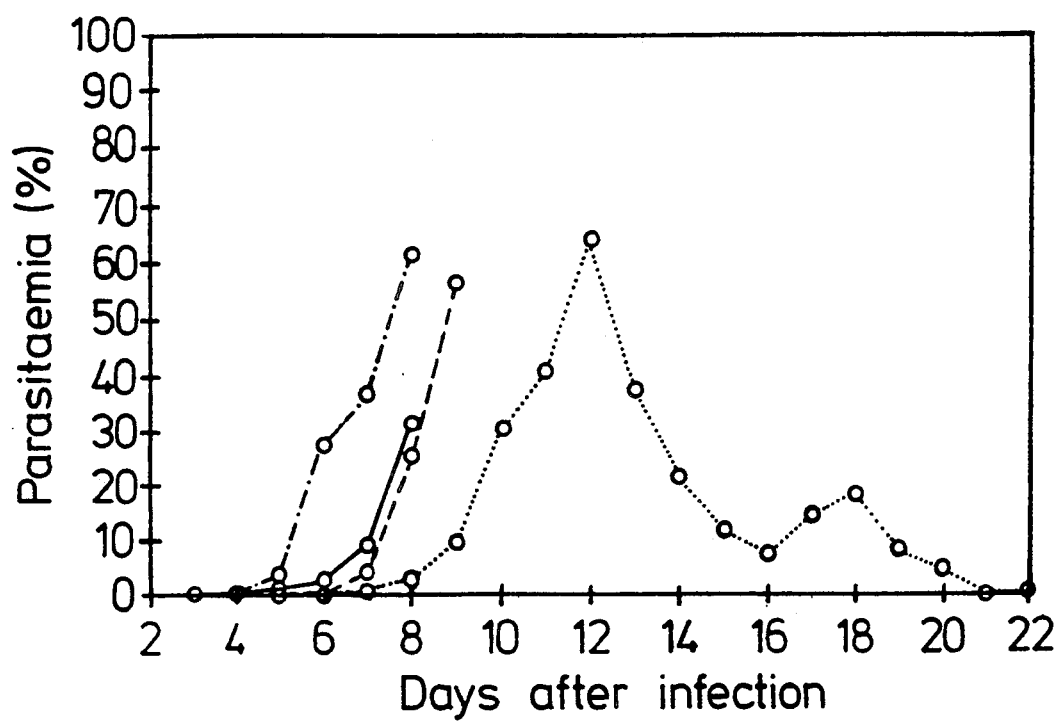
FIG. 1 depicts the course of a Plasmodium vinckei malaria in BALB/c mice after different treatments (n=6 for each treated group) given, once a day, 80 $\mu$g of chloroquine (o—o), 1×10$^4$U IFN$\gamma$ (o - - - o), a combination of both active substances (o . . . o) or as the control group phosphate buffered saline (PBS) plus murine albumin (o-.-.-.o) 3 days before till 7 days after the infection. The average values of the parasitaemias are shown.

According to the invention, therefore, it is proposed to use interferon plus at least one antimalarially active substance for preparing a pharmaceutical composition for the treatment of erythrocytic, clinical malaria. Unexpectedly, it has been discovered that the present invention makes it possible to carry out a lasting treatment of clinical malaria, i.e. malaria which can be diagnosed by known methods.

Surprisingly, it has also been found that the combined administration of interferon with at least one antimalarially active substance led to a synergistic increase in activity in the treatment of clinical malaria and a lasting cure for the disease, free from recurrence, without any formation of resistance in non-immune individuals.

It was also found, surprisingly, that the administration of the drug combination according to the invention, in addition to the synergistic antimalarial effect, imparts an additional rapid immunity to the particular pathogen, even after a single infection with this pathogen.

Thus, the use of the drug combinations according to the invention to treat clinical malaria achieves a multiple advantage: a lasting curative treatment of the clinically manifest infection without the formation of resistance in non-immune individuals and the rapid formation of immunity to the pathogen in question.

In contrast to the use of the drug combination according to the invention, when administering the particular individual substances (antimalarially active substance or interferon), hitherto it has only been possible to achieve a slight extension in the survival time compared with the placebo-treated group or, if the combination of IFN-γ plus antimalarial agent was prescribed, it was proposed for use only in the non-clinical prepatent phase.

In some cases, when the antimalarial substance, e.g. chloroquine, was administered in high does post infectionem, this treatment resulted in survival of a malaria infection; however, no protection was conferred against reinfection with the same strain of pathogen.

Reinfection experiments with the group treated with the drug according to the invention, on the other hand, showed that the blood of this group was not infectious and that protection was obtained against reinfection by the same strain of pathogen.

Suitable antimalarial substances for the pharmaceutical preparation according to the invention include the known synthetic, semisynthetic and naturally occurring active substances such as those in the above-mentioned groups of compounds, compounds and individual active substances and in the form of combinations thereof.

The interferons to be used according to the invention include the naturally occurring, synthetic and semisynthetic type I and type II interferons and those prepared by genetic engineering using DNA-recombination (interferons α, β and γ), interferon γ (IFN-γ) being preferred.

The IFN-γ to be used for the purposes of the invention can be prepared by the known methods of conventional cell cultures of animal or human origin, e.g. according to (Benjamin et al., *Proc. Natl. Acad. Sci. USA.* 79:5379–5383 (1982); Yip et al., *Proc. Natl. Acad. Sci. USA* 78:1601–1605 (1981); Yip et al., *Proc. Natl. Acad. Sci USA* 79:1820–1824 (1982)), or by the known technology of DNA-recombination, e.g. according to GRAY et al., *Nature* 295:503–508 (1982); Rinderknecht et al., *J. Biol. Chem.* 259:6790–6797; Devos et al., *Nucl. Acids Res.* 10:2487–2501 (1982); Gray et al., *Proc. Natl. Acad. Sci. USA* 80:5842–5846 (1983) or according to EP-B-77 670, EP-A-271,824 or according to Taniguchi et al., *Nature* 285:547–549 (1980); Goeddel et al., *Nature* 287:411–416 (1980)); EP-B-95702, EP-A-280,033.

For the purposes of the invention it is preferable to use IFN-γ, particularly an IFN-γ which can be obtained by DNA-recombination using known methods.

It is well known to those of ordinary skill in the art that natural allelic variations occur specifically in the individual or in different populations and can be manifested by one or more different amino acids or by different nucleotides or DNA sequences. Variations or mutations of this kind, which may also be produced by the known methods of DNA recombination or by controlled mutagenesis, as described for example by P. W. Gray et al., 1982 loc. cit. and Devos et al., (1982), loc. cit., comprise single or multiple substitutions, deletions, additions, insertions or inversions. These IFN-γs are therefore included according to the invention.

For immunological reasons it is known to those skilled in the art that it is preferable to use species-specific active substances when using biologically active substances native to the body. For the species-specific use of interferon according to the invention it is therefore preferable to use interferon isolated from the particular species-specific tissues or the nucleic acids (RNA, DNA) isolated from the species-specific tissues or cells to produce the particular interferon by DNA recombination, but in particular it is preferable to use the polypeptide identical to the particular genuine interferon with the known biological spectrum of activity of interferon. Thus, for example, the interferon used for the purposes of the invention in human beings will preferably be an IFN-γ, more particularly a human IFN-γ.

The interferon according to the invention may be administered by means of the pharmaceutical or galenic formulations known and used by those skilled in the art for the particular method of administration, but preferably those used for parenteral administration, especially for intravenous, intramuscular, subcutaneous, intracutaneous, intraarticular, intrathecal, intraperitoneal infusion or injection, including continuous infusions or intermittent infusions with the pumps available to those skilled in the art, or the administration by means of micro-encapsulated preparations, e.g. based on liposomes, e.g. according to EP-A-213,523.

For preparing a ready-to-use solution for the administration of interferon according to the invention, one may use the aqueous infusible and injectable solutions known for this purpose, optionally together with the excipients, carriers and/or stabilizing substances known in the art. A ready-to-use solution for the purposes of the invention may for example be prepared by dissolving highly purified interferon in "water for injections" or in phosphate-buffered physiological saline solution (pH 7 to 7.5), optionally supplemented with Tween and/or gelatine or an albumin, before administration, the solution being transferred under sterile conditions into suitable containers (e.g. syringes, ampoules, bags).

The quantity of interferon to be administered for the purposes of the invention will be determined in accordance with the dosages known in the art, the severity of the disease, the response rate and the further course of the disease and side effects. Generally speaking, the dosage must be adjusted according to individual criteria.

The antimalarially active synthetic, semisynthetic or naturally occurring substances to be used according to the invention, at least one of which is combined with animal or human interferon, may be any of the known antimalarially active agents described, advantageously compounds from the group comprising the 9-aminoacridines, 4-aminoquinolines, 8-aminoquinolines, biguanides, diaminopyrimidines, quinine salts, sulphonamides, sulfanilamides, antibiotics (such as tetracyclines) or sulphones (such as dapsone or 4,4'-diaminodiphenyl-sulphone), e.g. chloroquine[(7-chloro-4-(4-diethylamino-1-methylbutylamino)-quinoline].

The method of administration and dosage will depend on the therapy plans known for the above-mentioned antimalarial agents, including also liposome-based microencapsulated antimalarial substances, e.g. according to EP-A-213,523 or EP-A-152,379 and also, for example, according to EP-A-354,442 or EP-B-56,781, to name just some of the numerous published patent literature.

The drug according to the invention based on at least one substance with an antimalarial activity plus an interferon can be used either by simultaneous administration of the two different types of active substance (antimalarial substance, interferon) or by consecutive or sequential administration by suitable route, the individual active substances being provided and administered either separately, e.g. in the form of a "kit-of-parts" or directly together, in terms of space and time. The active substance components which are present separately or either indirectly or directly together may be provided both as dry substances and as solutions, whilst microencapsulated forms are also possible in which the active substance components may be used directly together, indirectly as a liposome mixture or as separate systems for administration. It is advantageous for the two active substance components, the antimalarial drug and interferon, to be administered simultaneously.

It is intended that any animal may be treated with the pharmaceutical compositions of the present invention. Preferably, such animal is a human, however, the invention is not intended to be so limited.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. All patents and publications cited herein are incorporated by reference herein in their entirety.

EXAMPLE

A. Infection:

In all the experiments, female BALB/c mice 8 to 10 weeks old (Federal Health Institute Berlin) were used. The mice were infected with *P. vinckei* by intraperitoneal injection of $10^5$ parasitized erythrocytes suspended in 100 μl of phosphate buffered saline (PBS). For the reinfection experiments, *P. vinckei* and *P. berghei* were administered in the same way. Three days post infectionem, thin blood slides were prepared and stained with giemsa dye in order to determine the parasitaemia. The statistical analysis was carried out using the Wilcoxon test.

B. Treatment with chloroquine:

Groups of six mice infected with *P. vinckei* were treated on the day of infection with varying doses of chloroquine (Bayer, Leverkusen) in the form of a single intraperitoneal administration in the dosage range from 40 μg to 300 μg per mouse, diluted in 100 μl PBS. The control animals were given only PBS. The untreated animals (control animals) succumbed to the infection after an average time of 8 days. In the mice treated with a high dosage of 300 μg of chloroquine, only a low and delayed parasitaemia was observed and all the mice survived. By comparison, of the group given 120 μg of chloroquine, only two mice survived. All the mice treated with 40 or 80 μg of chloroquine died within 11 days post infectionem. A significant ($P<0.05$) increase in the survival time compared with the controls was observed in the mice treated with 80 μg of chloroquine, but not in those given 40 μg of chloroquine. Therefore, 80 μg (4 mg/kg) was chosen as the subcurative chloroquine treatment for the remaining investigations.

C. Treatment with IFN-γ:

In this group (n=6) the mice were treated with recombinant murine IFN-γ from *E. coli* (Genentech Inc. South San Francisco, Calif., or produced according to Gray, et al., (*Proc. Natl. Acad. Sci.* USA 80:5842-5846 (1983)) with a specific activity of $1.9 \times 10^7$ U/mg of protein dissolved in PBS containing 0.1% murine albumin. The daily intraperitoneal administrations of 100 μl with either $10^4$ U IFN-γ per mouse or $5 \times 10^4$ U IFN-γ per mouse were given over a period of 11 successive days, the treatment beginning 3 days before infection and ending 7 days after infection. The control animals were given PBS plus murine albumin (0.1%). The administration of IFN-γ significantly ($P<0.05$) delayed the outbreak of any clear parasitaemia and increased the survival time. In those mice which were given $1 \times 10^4$ U IFN-γ per day over a period of 11 days, the survival time was increased by only 1 day compared with the controls and all the mice died.

However, of those mice which were given $5 \times 10^4$ U IFN-γ per day, three of the six mice survived the *P. vinckei* malaria.

D. Treatment with IFN-γ plus chloroquine:

This third group of mice were treated with $1 \times 10^4$ U IFN-γ per day (as described in C.) in conjunction with 80 μg of chloroquine (as described in B.) and compared both with the mice which were given these two substances separately and with the control group (FIG. 1).

The control mice died after 9.0 days (average), the chloroquinetreated mice died after 10.25 days (average) and the IFN-γ treated mice died 10.0 days (average) post infectionem. In the group given the combined treatment, the parasitaemia only became obvious on day 5 or day 6 after the infection, as against day 3 or day 4 in the other groups. In the mice treated with the combination, the peak parasitaemia was achieved on day 12.

One out of six mice given the combined treatment died on day 11. In three of the five surviving mice there was a second smaller peak of parasitaemia which appeared approximately 18 days after the infection. On day 22 all five mice had negative findings and remained free from parasites for at least five weeks (until the reinfection experiments).

E. Reinfection experiments:

Those mice which survived the *P. vinckei* malaria thanks to the combined treatment with IFN-γ and chloroquine as described under D., were reinfected with the same strain of *P. vinckei* five to ten weeks after the first infection.

None of the mice developed any recognizable parasitaemia within an evaluation period of more than ten weeks. However, crisis forms were visible under the microscope. The blood from these mice was then injected into original, uninfected mice, whereupon no parasitaemia developed. By contrast, those mice which had been cured with high doses of chloroquine (as described under B.) showed no resistance to reinfection with the same strain.

In order to determine whether this immunity achieved with the combined treatment is specific to the strain, the surviving mice treated with the combination were infected either with *P. vinckei, P. berghei* or with a combination of *P. vinckei* plus *P. berghei* in this sequence and compared with control mice infected with the same parasites.

With regard to the course of the parasitaemia, the immune mice infected with *P. berghei* or *P. vinckei* plus *P. berghei* showed a similar tendency compared with a control group of original BALB/c mice infected with *P. berghei*. The groups of original mice which had been infected either with *P. vinckei* or with both strains showed an earlier increase in parasitaemia, caused by the unhindered multiplication of *P. vinckei*, (Table 1).

Table 1: Reinfection experiments. Course of the average parasitaemias (range) in three groups of original mice which were infected with either *Plasmodium berghei anka* or *Plasmodium vinckei* or a combination of *P. berghei* plus *P. vinckei* (n=6 in each case) and in three groups of immune mice which were infected with either *P. berghei* or *P. vinckei* or a combination of *P. berghei* plus *P. vinckei* (n=6 in each case).

| Days after infection | 4 | 5 | 6 |
|---|---|---|---|
| original mice infected with *P. berghei* | 1% (0.1–3) | 3.5% (1–5) | 5.5% (4–7) |
| immune mice infected with *P.berghei* | 0.5% (0.1–1) | 3% (2–6) | 6.5% (5–11) |
| original mice infected with *P. vinckei* | 1% (0.5–2) | 5% (3–10) | 16% (8–23) |
| immune mice infected with *P. vinckei* | 0% (0–0) | 0% (0–0) | 0% (0–0) |
| original mice infected with *P. berghei* and *P. vinckei* | 3% (3–4) | 9% (7–10) | 12.5% (11–14) |
| immune mice infected with *P. berghei* and *P. vinckei* | 0.5% (0.1–2) | 4.5% (2–7) | 8.5% (5–11) |

From the foregoing description, one skilled in the art can easily ascertain the essential characteristics of this invention, and without departing from the spirit and scope thereof, can make various changes and modifications of the invention to adapt it to various usages and conditions.

I claim:

1. A method for treating malarial infections caused by protozoa of the genus Plasmodium, when such infections have entered the erythrocytic clinical phase, comprising administering to an animal having merozoite infected erythrocytes, a combination of gamma-interferon and at least one additional substance having antimalarial activity selected from the group consisting of 9-aminoacridines, 4-aminoquinolines, 8-aminoquinolines, biguanides, diaminopyrimidines, quinine salts, sulphonamides, sulfanilamides, tetracycline, and sulphones, the components of said combination being administered either simultaneously, consecutively, or sequentially, in an amount effective to destroy said erythrocytic merozoites.

2. The method according to claim 1, characterized in that said antimalarial substance is a 4-aminoquinoline.

3. The method according to claim 2, characterized in that the antimalarial substance is chloroquine [(7-chloro-4-(4-diethylamino-1-methylbutylamino)-quinoline].

4. The method according to claim 1, characterized in that the interferon is species-specific.

5. The method according to claim 1, characterized in that the interferon is a human interferon.

6. The method according to claim 1, characterized in that the interferon is an animal interferon.

* * * * *